US005494909A

United States Patent [19]

Kóbor et al.

[11] Patent Number: 5,494,909

[45] Date of Patent: Feb. 27, 1996

[54] SUBSTITUTED OXAZINOISOQUINOLINE DERIVATIVES, PHARMACEUTICAL COMPOSITIONS CONTAINING THEM AND PROCESS FOR PREPARING SAME

[75] Inventors: Jenő Kóbor; Lászl'' Lázár; Imre Huber; Judit Árva, all of Szeged; Lászl'' Szporny, Budapest; Béla Kiss, Budapest; Egon Kárpáti, Budapest; Éva Pálosi, Budapest; Zsolt Szombathelyi, Budapest; Ádám Sarkadi, Budapest; Anikó Gere, Budapest; Mihály Bodó, Budapest; Katalin Csomor, Budapest; Judit Laszy, Nagykovácsi; Zsolt Szentirmai, Budapest; Erzsébet Lapis, Budapest; Sándor Szabó, Budapest; Gábor Bernáth; Ferenc Fülöp, both of Szeged, all of Hungary

[73] Assignee: Richter Gedeon Vegyeszeti Gyar RT., Budapest, Hungary

[21] Appl. No.: 244,736

[22] PCT Filed: Dec. 11, 1992

[86] PCT No.: PCT/HU92/00053

§ 371 Date: Jul. 20, 1994

§ 102(e) Date: Jul. 20, 1994

[87] PCT Pub. No.: WO93/12118

PCT Pub. Date: Jun. 24, 1993

[30] Foreign Application Priority Data

Dec. 12, 1991 [HU] Hungary ............................ P 91 03906

[51] Int. Cl.$^{6}$ ......................... A61K 31/47; C07D 265/14

[52] U.S. Cl. ............................................ 514/230.2; 544/89

[58] Field of Search ............................. 514/230.2; 544/89

[56] References Cited

U.S. PATENT DOCUMENTS 4,605,653 8/1986 Bernath et al. ......................... 514/226

*Primary Examiner*—Yogendra N. Gupta

*Attorney, Agent, or Firm*—Herbert Dubno; Jonathan Myers

[57] ABSTRACT

New compounds with the ability to inhibit calcium uptake in the brains of mammals are disclosed of the Formula (I)

(I)

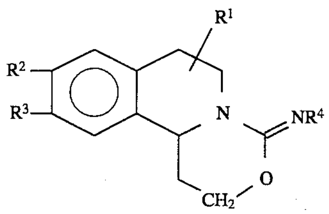

wherein $R^1$ is hydrogen, $C_1$ to $C_4$ alkyl, phenyl, or phenyl-$C_1$ to $C_4$ alkyl;

one of $R^2$ and $R^3$ is $C_1$ to $C_4$ alkoxy and the other one is phenyl-$C_1$ to $C_4$ alkoxy optionally substituted by $C_1$ to $C_4$ alkyl in the aromatic nucleus; and $R^4$ is phenyl optionally substituted by $C_1$ to $C_4$ alkyl in the aromatic nucleus, or their solvates, individual optically active and geometric isomers, mixtures of such isomers, as well as pharmaceutically acceptable acid addition salts thereof. The compounds of the Formula (I) are capable of inhibiting calcium uptake to brain cells and have a protective effect on hypobaric hypoxia.

6 Claims, No Drawings

SUBSTITUTED OXAZINOISOQUINOLINE DERIVATIVES, PHARMACEUTICAL COMPOSITIONS CONTAINING THEM AND PROCESS FOR PREPARING SAME

FIELD OF THE INVENTION

This application is 371 of PCT/HU92/00053 filed on Dec. 11, 1992.

This invention relates to novel, therapeutically active substituted oxazinoisoquinoline derivatives of the formula (I)

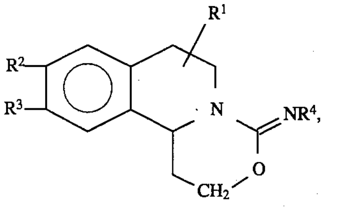

wherein

- $R^1$ is hydrogen, $C_{1-4}$alkyl, phenyl or phenyl-$C_{1-4}$alkyl;
- one of $R^2$ and $R^3$ is $C_{1-4}$alkoxy and the other one is phenyl-$C_{1-4}$alkoxy group optionally substituted by $C_{1-4}$alkyl in the aromatic nucleus; and
- $R^4$ is phenyl optionally substituted by $C_{1-4}$alkyl in the aromatic nucleus, and their solvates, their individual optically active and geometric isomers, mixtures of such isomers as well as acid addition salts of these compounds formed with inorganic and organic acids.

Furthermore, the invention relates to pharmaceutical compositions being useful for the prevention and treatment of brain injuries; as well as to a process for preparing the compounds of the invention and to a method for treatment and prevention of brain injuries in mammals.

BACKGROUND OF THE INVENTION

Ischaemia-induced neurochemical alterations are related to ion fluxes through the cell membranes and subcellular membranes, respectively. However, the factor of key importance in the development of an ischaemia-induced injury is the increase in the intracellular free calcium level. The ceasing of energy supply for the cell causes the loss of the cellular calcium homeostatis. The release of potassium elicits membrane depolarization inducing the opening of the potential-dependent calcium channels. The entry of calcium to the cell partially proceeds through these potential-dependent channels. On the other hand, the increase in the sodium permeability of the membrane induces an intense release of excitatory amino acids (glutamate, aspartate). The glutamate released activates the receptor-dependent calcium channels, permitting an additional calcium influx into the cell [J. Cereb. Blood Flow Metab. 9, 127 (1989)].

The influx of calcium to the cell (pre- and postsynaptic calcium influx) may initiate catabolic reactions. The increased intracellular calcium level elicits reactions significantly influencing the functions and integrity of the cell. (Such reactions are e.g.: lipolysis, proteolysis, decomposition of microtubules, excessive protein phosphorylation) [Central Nervous System Trauma, Chapter 37, pages 513–532 (1984)].

The mechanisms playing a role in the neurotoxicity of veratrine are similar to the ischaemia-induced neurochemical changes. Veratrine significantly increases the tetrodotoxine-sensitive (TTX-sensitive) sodium permeability. The membrane depolarization caused by a persistent sodium influx leads to calcium influx and intracellular calcium release.

In addition, veratrine-induced depolarization causes an intense release of glutamate and aspartate [Neurosci. Lett. 121, 251 (1991); and Brain Res. 528, 212 (1990)].

Thus, the inhibition of sodium and calcium channels may play an important role in the mechanism of action of cerebro-protective compounds. The use of the sodium channel blocker TTX proved to have an advantageous effect in the protection against ischaemic injury (see the last two references cited).

Therefore, compounds diminishing the pre- or postsynaptic calcium uptake or altering the calcium sequestration in the intracellular sites may bear a high therapeutic importance.

At present, calcium antagonists are used for the treatment of ischaemic injuries mainly on the basis of their vascular effects; however, it seems to be more and more important to realize that compounds with such a mechanism of action have to exert their antihypoxic, anti-ischaemic effects by inhibition of the calcium influx to the neurons.

Non-competitive NMDA antagonists such as MK-801 (disocilpine) [(+)-5-methyl-10,11-dihydro-5H-dibenzo[a,d] cyclohepten-5,10-imine], which inhibit the excitatory amino acid receptor-dependent calcium channels and, consequently, protect from the increase in the intracellular calcium level [Stroke 21 (Suppl. IV), IV. 72-IV. 77 (1990); as well as J. Cereb. Blood Flow Metab. 9, 127 (1989)], are of therapeutic importance.

SUMMARY OF THE INVENTION

Surprisingly, it has been found that the compounds of the formula (I) according to the invention are capable of inhibiting the calcium uptake into synaptosomes; thus, they are suitable to protect the organism against calcium-mediated injuries (e.g. ischaemia- and hypoxia-induced injuries) and the complications arising therefrom, respectively.

The synthesis of compounds of similar structure is reported in Heterocycles 20, 1325 (1983); however, the pharmaceutical action of the compounds prepared is not mentioned. Substances of similar structure but with an 1-hydroxymethyl substituent are described in the Hungarian patent specification No. 191,301; these latter compounds possess an anticonvulsive effect being substantially different from that of the compounds according to the present invention.

According to an other aspect of the invention, there is provided a process for the preparation of compounds of the formula (I) as well as their acid addition salts, which comprises reacting an isoquinoline derivative of the formula (II)

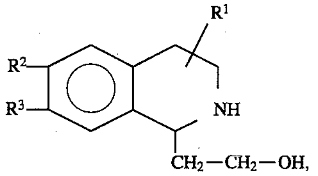

wherein $R^1$, $R^2$ and $R^3$ are as defined at formula (I), with an isocyanate or isothiocyanate, respectively, of the formula x is oxy as defined at formula (I) and X means oxygen or sulfur, respectively; or with a $C_{1-4}$alkyl dithiocarbamate bearing an $R^4$ substituent on its nitrogen atom, to give isoquinoline derivatives of the formula

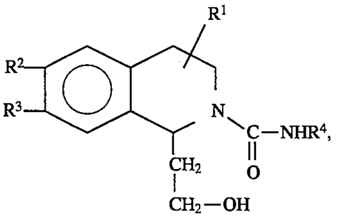

(III)

or

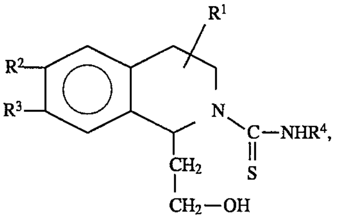

(IV)

respectively, wherein $R^1$, $R^2$, $R^3$ and $R^4$ are as defined at formula (I); then a) reacting a thus-obtained thiocarbamoylisoquinoline derivative of the formula (IV), wherein $R^1$, $R^2$, $R^3$ and $R^4$ are as defined at formula (I), with a $C_{1-4}$alkyl halide; or b) treating a thus-obtained carbamoylisoquinoline derivative of the formula (III), wherein $R^1$, $R^2$, $R^3$ and $R^4$ are as with a dehydrating agent;

then, if desired, reacting the thus-obtained compound of the formula (I), wherein $R^1$, $R^2$, $R^3$ and $R^4$ are as defined at formula (I), with an acid to give an acid addition salt; and/or treating a compound of the formula (I), cancel $R^1$, $R^2$, $R^3$ and $R^4$ are as defined at formula (I), obtained in the form of its acid addition salt, with a base to liberate the free basic form.

The isoquinoline derivatives of the formula (II) used as starting substances are also novel compounds, which may be prepared from the known 3,4-dihydroisoquinoline derivatives of the formula

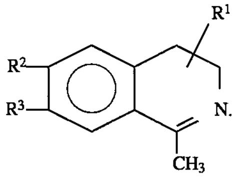

(V)

For this purpose, firstly a 3,4-dihydroisoquinoline derivative of formula (V), wherein $R^1$, $R^2$ and $R^3$ are as defined at formula (I), is reacted with formaldehyde or its hydrate or a trimeric or polymeric derivative thereof, preferably in the presence of a base, then the 1-hydroxy-ethyl-3,4-dihydroisoquinoline derivative of the formula

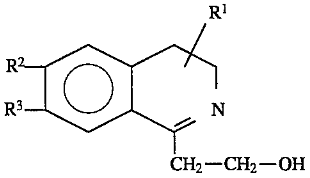

(VI)

obtained, wherein $R^1$, $R^2$ and $R^3$ are as defined at formula is reduced.

When preparing the compounds of the formula (VI) alkaline metal alkoxides and hydroxides may be used as bases; sodium methoxide, sodium ethoxide and sodium hydroxide are preferably used.

According to a preferred embodiment 2.5 moles of paraformaldehyde in methanolic suspension are added to a solution of 1 mole of 3,4-dihydroisoquinoline derivative of formula (V) in methanol, and subsequently a freshly prepared ethanolic sodium ethoxide solution is added in an amount sufficient to dissolve the suspension. Then the reaction mixture is stirred at room temperature for about 6 hours and evaporated. The appropriately substituted 1-hydroxyethyl-3,4-dihydroisoquinoline derivative of the formula (VI) is obtained as an evaporation residue.

The subsequent reduction may be carried out by using a complex metal hydride or catalytic hydrogenation. Sodium borohydride dissolved in an alkanol or aqueous alkanol medium may preferably be used as a complex metal hydride. The catalytic hydrogenation may advantageously be performed by using a palladium-on-carbon or platinum-on-carbon catalyst. In the latter case, an alkanol is preferably used as solvent.

In the course of the reduction, mixtures of diastereomers are formed, the isomer ratio of which depends on the reducing agent. The components of these mixtures can be separated by using well known methods, preferably fractional crystallization.

If desired, the compounds of the formula (II) obtained may be converted to their salts.

The reduction step is preferably carried out in such a way that, after dissolving 1 mole of a 1-hydroxyethyl-3,4-dihydroisoquinoline derivative of the formula (VI) in methanol, about 4 moles of sodium borohydride are added to the solution in small portions while cooling with ice. After the termination of the reaction the mixture is evaporated to give an appropriately substituted isoquinoline derivative of formula (II).

The calcium uptake-inhibitory effect of the compounds of the formula (I) according to the invention was studied on synaptosomes prepared from rat brain by using a method described in J. Neurochem. 32, 700 (1982) in the following manner.

Wistar rats weighing 180 to 200 g were decapitated and the brains were collected in ice-cold physiological saline, the cortex was removed and purified from the white matter. The tissue was homogenized by a glass-teflon potter in 10 volumes of a saccharose solution of 0.32 moles/liter concentration. The homogenate was centrifuged at 1000×g in a Janetzki K-70 centrifuge at 4° C. for 10 minutes, the supernatant was centrifuged at 12000×g in a Hitachi CR-26H centrifuge at 4° C. for 20 minutes. The sediment was suspended in a saccharose solution of 0.32 moles/liter concentration, then the protein content of the preparation was adjusted to 20 mg/ml.

Components of the solution used for incubation were as follows:

a) For investigation of the potassium-stimulated calcium uptake: 112 mmoles/l of sodium chloride, 5 mmoles/l of potassium chloride, 1.3 mmoles/l of magnesium chloride, 1.2 mmoles/l of sodium dihydrogen phosphate, 1.2 mmoles/l of calcium chloride, 10 mmoles/l of glucose and 20 mmoles/l of tri(hydroxymethyl)aminomethane (TRIS);

b) For investigation of the veratrine-stimulated calcium uptake: 132 mmoles/l of sodium chloride, 5 mmoles/l of potassium chloride, 1.3 mmoles/l of magnesium chloride, 1.2 mmoles/l of sodium dihydrogen phosphate, 1.2 mmoles/l of calcium chloride, 10 mmoles/l of glucose and 20 mmoles/l of TRIS.

Incubation solution was saturated with oxygen containing 5% by volume of carbon dioxide until reaching a pH value of 7.4. The test compounds and the synaptosome preparation in an amount corresponding to 1 mg of protein were added into the incubation solution. The final volume of incubation was 1 ml. The samples were pre-incubated at 37° C. for 20 minutes.

The calcium uptake was initiated by addition of a $45_{CACl2}$solution of 2.8 kBq (75 nCi) activity. Potassium chloride was used in a concentration of 60 mmoles/l for the investigation of potassium-stimulated calcium uptake; sodium chloride was added in the same concentration to the control samples. Veratrine was used in a concentration of 20 μmoles/1 for investigating the veratrine-stimulated calcium uptake.

The incubation time was 20 seconds. The reaction stopped by adding 5 ml of a stopping solution containing 120 mmoles/l of sodium chloride, 5 mmoles/l of potassium chloride, 5 mmoles/l of EGTA [ethylene glycol bis(β-aminoethyl)ether-N,N, N',N'-tetraacetic acid]and 20 mmoles/l of TRIS (pH 7.4).

The samples were filtered through a Whatman GF/C filter and washed twice with 5-5 ml of a washing solution containing 132 mmoles/l of sodium chloride, 5 mmoles/l of potassium chloride, 1.3 mmoles/l of magnesium chloride, 1.2 mmoles/l of calcium chloride and 20 mmoles/l of TRIS (pH 7.4)

After placing the filter disks in glass cuvets, 10 ml of scintillation cocktail [containing 1000 ml of toluene, 400 ml of abs. ethanol, 10 ml of dioxane, 6 g of 2,5-diphenyloxazole and 0.15 g of 1,4-bis(5-phenyl-2-oxazolyl)benzene] and the radioactivity of the samples was measured by using an 1219 Rackbeta type liquid scintillation spectrophotometer (product of LKB Wallace Company).

The $IC_{50}$ values shown in Table 1 were determined by measuring the concentration-effect relation of the compounds.

TABLE 1

Inhibition of the stimulated calcium uptake

| | Inhibition of | |
|---|---|---|
| Name/code No. of compound | Potassium-stimulated Ca untake | Veratrine-stimulated Ca uptake |
| | $IC_{50}$ (μmole/l) | |
| 1507136 | 23.9 | 0.29 |
| nimodipine | 208.0 | 6.7 |
| cinnarizine | 71.6 | 1.0 |
| flunarizine | 22.6 | 1.3 |

Note: The compound No. 1507136 is 9-benzyloxy-10-methoxy-4-(p-tolylimino)-1,6,7,11b-tetrahydro-2H,4H-1,3-oxazino-[4,3-a]isoquinoline hydrochloride
Nimopidine [isopropyl 2-methoxyethyl 1,4-dihydro-2,6-dimethyl-4-(m-nitrophenyl)-3,5-pyridinedicarboxylate], cinnarizine [1-trans-cinnamyl-4-(diphenylmethyl)piperazine] as well as flunarizine [1-cinnamyl-4-[bis(4-fluorophenyl)-methyl]-piperazine] were used as reference drugs.

It is obvious from the data of Table 1 that the compounds according to the invention possess a calcium uptake-inhibitory effect. In comparison to nimodipine, their effect on the calcium uptake induced by either potassium or veratrine is much stronger. The potassium-induced calcium uptake inhibitory effect of compound No. 1507136 exceeds that of cinnarizine. The substance tested blocked also the veratrine-induced calcium uptake to a higher degree than flunarizine did.

The antihypoxic effect of the target compounds was studied on genetically hypertensive rats (SHR), which are particularly sensitive to hypoxic insults. Male rats weighing 210 to 230 g each were used for these experiments.

The hypobaric hypoxia test

The experimental animals were placed in pairs in a desiccator of 6 liters volume one hour after administration of the compound to be tested. The pressure in the desiccator was decreased to 22.66 kPa (170 mmHg) during 20 seconds. The time elapsing from this point until the last respiratory movement was measured. An animal was considered to be protected when its survival time was by 30% longer in comparison with the control group. The $ED_{50}$ value (i.e. the dose being effective in 50% of the animals) together with the corresponding fiducial limits was calculated by using the probit analysis from the percentage of the animals protected.

TABLE 2

The hypobaric hypoxia test

| Name/code No. of compounds | $ED_{50}$ (mg/kg) |
|---|---|
| 1507136 | 8.0 |
| nimodipine | 8.0 |
| flunarizine | 50.0 |

It can be stated from the results shown in Table 2 that the effect of compounds of the present invention is equal to that of nimodipine under severe hypoxic conditions (hypobaric hypoxia) and is significantly better than that of flunarizine.

Based on the above investigations the compounds according to the invention can therapeutically be used mainly against brain injuries of severely hypoxic origin.

The compounds of the invention can be used orally or parenterally either alone or in the form of pharmaceutical compositions. These compositions may be mainly tablets, capsules, powders, syrups, injectable solutions or suppositories. The daily doses of the active compounds are between 0.1 and 50 mg/kg of body weight; however, this limit value may be exceeded depending on the severity of the pathological state to be treated since the toxicity of compounds of the invention is low (e.g. the oral $LD_{50}$ value of the compound No. 1507136 is 1400 mg/kg of body weight). The daily dose of the active compound may be administered once or in subdoses to the patient to be treated.

The invention also relates to a method for prevention and treatment of brain injuries of hypoxic origin. This method comprises administering a therapeutically effective amount of an active agent of the formula (I) or a pharmaceutically acceptable acid addition salt thereof to the patient.

The invention is illustrated in detail by the aid of the following non-limiting Examples. The identity of identical products prepared by various methods was confirmed by their IR spectra and mixed melting points.

EXAMPLE 1

A mixture containing 0.01 mole of a 1-(2-hydroxy-ethyl)-6,7-disubstituted-1,2,3,4-tetrahydroisoquinoline of formula (II) and 0.01 mole of an isothiocyanate of formula $R^4$-CNS in 50 ml of benzene is refluxed under nitrogen for 1 hour. After evaporation of the solvent the corresponding isoquinoline derivative of formula (IV) is obtained in crystalline form in a yield of 85-94%.

EXAMPLE 2

A mixture of 0.01 mole of a 1-(2-hydroxyethyl)-6,7-disubstituted-1,2,3,4-tetrahydroisoquinoline, 0.01 mole of a $C_{1-4}$alkyl dithiocarbamate bearing an $R^4$ substituent on the nitrogen atom and 50 ml of ethanol is refluxed for 3-4 hours.

After evaporating the solvents, the corresponding compound of the formula (IV) is obtained as crystals in a yield of 76-92%.

The following compounds were prepared by following the processes described in Examples 1 and 2:

6-benzyloxy-1-(2-hydroxyethyl)-7-methoxy-2-(p-tolylthiocarbamoyl)- 1,2,3,4-tetrahydroisoquinoline, m.p.: 181°–182° C. (after recrystallization from methanol);

7-benzyloxy-1-(2-hydroxyethyl)-6-methoxy-2-(p-tolylthiocarbamoyl)- 1,2,3,4-tetrahydroisoquinoline, m.p.: 121°–123° C. (after recrystallization from ethanol).

EXAMPLE 3

A mixture containing 0.01 mole of a 1-(2-hydroxy-ethyl)-6,7-disubstituted-1,2,3,4-tetrahydroisoquinoline of the formula (II) and 0.01 mole of an isocyanate of the formula $R^4$—CNO in 50 ml of benzene is refluxed for 1 hour. After evaporating the solvent the corresponding compound of the formula (III) is obtained as crystals in a yield of 85–92%.

EXAMPLE 4

After adding 1.7 g (0.012 mole) of methyl iodide and 20 ml of methanol to 0.01 mole of a 1-(2-hydroxyethyl)-6,7-di-substituted- 2-thiocarbamoyl-1,2,3,4-tetrahydroisoquinoline of the formula (IV), the reaction mixture is stirred for 3–4 hours, then the solvent is evaporated. The residue is stirred with 20 ml of methanolic potassium hydroxide solution of 3 moles/liter concentration until the complete removal of methyl mercaptan. After evaporating the mixture to dryness a little water is added to the residue and then extracted 4 times with 20 ml of chloroform each. After combining, the extracts are dried and evaporated to give the corresponding oxazine derivative of the formula (I) in a yield of about 70– 86%.

In some cases the working-up of the reaction mixture is modified: when the product precipitates in a crystalline form after evaporation to dryness and addition of a little water, it is separated by filtration.

EXAMPLE 5

After adding 10 ml of thionyl chloride to 0.005 moles of 1-(2-hydroxyethyl)-6,7-disubstituted-2-carbamoyl-1,2,3, 4tetrahydroisoquinoline of the formula (III) prepared as described in Example 3, the reaction mixture is allowed to stand overnight. After evaporating the excess of thionyl chloride, the residue is dissolved in a little water under cooling, neutralized by adding sodium hydrogen carbonate, then extracted with chloroform. After drying and evaporating the extract, the corresponding oxazine derivative of the formula (I) is obtained in crystalline form in a yield of about 65– 70%.

EXAMPLE 6

After adding 10 ml of phosphorous oxychloride to 0.005 moles of a 1-(2-hydroxyethyl)-6,7-disubstituted-2-carbamoyl-1,2,3,4-tetrahydroisoquinoline of the formula (III) prepared as described in Example 3, the process described in Example 5 is followed to obtain a yield of 58%.

By reacting with an acid, the compounds of the formula (I) obtained in the form of free base can be converted to their acid addition salts. The hydrochloride may preferably be formed by reacting the free base with a solution of hydrogen chloride in ethanol.

The following compounds were prepared by following the process described in Examples 4–6:

9-benzyloxy-10-methoxy-4-(p-tolylimino)-1,6,7,11b-tetrahydro- 2H,4H-1,3-oxazino[4,3-a]isoquinoline hydrochloride, m.p.: 155°–158° C. (after recrystallization from a mixture of ethanol and ether);

10-benzyloxy-9-methoxy-4-(p-tolylimino)-1,6,7,11b-tetrahydro- 2H,4H-1,3-oxazino[4,3-a]isoquinoline hydrochloride, m.p.: 139°–143° C. (after recrystallization from a mixture of ethanol and ether).

EXAMPLE 7

Preparation of tablets containing 5 or 50 mg, respectively, of active ingredient each Tablets with a weight of 150 mg or 300 mg each, respectively, containing the components listed hereinafter are prepared by using known methods of wet granulation and compression.

| Components | Amounts (mg) in the tablet containing | |
|---|---|---|
| | 5 mg of active agent | 50 mg of active agent |
| Active ingredient | 5 | 50 |
| Gelatine | 3 | — |
| Polyvidone (polyvinyl-pyrrolidone) | — | 6 |
| Magnesium stearate | 2 | 3 |
| Talc | 5 | 9 |
| Potatoe starch | 40 | 84 |
| Lactose | 95 | 148 |
| Total: | 150 mg | 300 mg |

We claim:

1. A compound of the formula

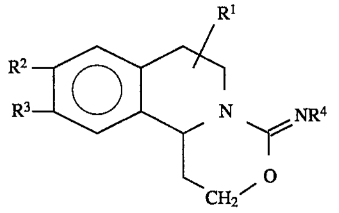

(I)

wherein $R^1$ is hydrogen, $C_{1-4}$alkyl, phenyl or phenyl-$C_{1-4}$alkyl;

one of $R^2$ and $R^3$ is $C_{1-4}$alkoxy and the other one is phenyl-$C_{1-4}$alkoxy optionally substituted by $C_{1-4}$alkyl in the aromatic nucleus; and $R^4$ is phenyl optionally substituted by $C_{1-4}$alkyl in the aromatic nucleus or a solvate, an individual optically active or geometric isomer thereof or a mixture of such isomers or a pharmaceutically acceptable acid addition salt thereof.

2. 10-Benzyloxy-9-methoxy-4-(4-tolylimino)-1,6,7,11b-tetrahydro- 2H,4H-1,3-oxazino[4,3-a]isoquinoline or a pharmaceutically acceptable acid addition salt thereof defined in claim 1.

3. 9-Benzyloxy-10-methoxy-4-(4-tolylimino)-1,6,7,11b-tetrahydro- 2H,4H-1,3-oxazino[4,3-a]isoquinoline or a pharmaceutically acceptable acid addition salt thereof define in claim 1.

4. A pharmaceutical composition for inhibiting the uptake of calcium, which comprises as active ingredient a therapeutically effective amount of a compound of the formula (I), or a solvate, an individual optically active or geometric isomer or a mixture of such isomers as defined in claim 1, or a pharmaceutically acceptable acid addition salt thereof in admixture with a pharmaceutically acceptable inert carrier.

5. A method of inhibiting the uptake of calcium to the brain of a mammal, characterized by administering to the mammal to be treated a therapeutically effective amount of a compound of the formula (I) as defined in claim 1 or a solvate, individual optically active or geometric isomer, or a mixture of isomers, or a pharmaceutically acceptable acid addition salt thereof.

6. The method defined in claim 5 for inhibiting the uptake of calcium to the brain of a mammal wherein the compound of the Formula (I) or a solvate, individual optically active or geometric isomer, or mixture of isomers, or a pharmaceutically acceptable acid addition salt thereof is administered to the mammal to treat or to prevent a brain injury resulting from hypoxia.

* * * * *